United States Patent [19]

Sato et al.

[11] Patent Number: 5,687,719
[45] Date of Patent: Nov. 18, 1997

[54] PULSE OXIMETER PROBE

[75] Inventors: Ikuo Sato, Tochigi; Keiichi Sugiura, Tokyo, both of Japan

[73] Assignees: Ikuo Sato, Tochigi; Nihon Kohden Corporation, Tokyo, both of Japan

[21] Appl. No.: 217,716

[22] Filed: Mar. 25, 1994

[30]     Foreign Application Priority Data

Mar. 25, 1993  [JP]  Japan ................. 5-014094 U

[51] Int. Cl.$^6$ ............................................. A61B 5/00
[52] U.S. Cl. ............................................. 128/633; 128/664
[58] Field of Search ............................... 128/633–634, 128/664–667

[56]           References Cited

U.S. PATENT DOCUMENTS 4,658,825  4/1987  Hochberg et al. ............... 128/634
4,938,218  7/1990  Goodman et al. ............... 128/633
5,377,675  1/1995  Ruskewicz et al. .............. 128/634

Primary Examiner—John P. Lacyk
Attorney, Agent, or Firm—Sughrue, Mion, Zinn, Macpeak & Seas

[57]               ABSTRACT

To determine the oxygen saturation and other parameters of blood flowing in a fetus positioned in the uterus by detecting the pulsation of the blood in the birthing process from the rupture of the water membrane to the delivery of the baby. An opening is formed near the distal end of a curved support member and both light-emitting portion and light-receiving portion are positioned in the opening as they are spaced apart by a specified gap in which the head of a fetus is rested for detecting the pulsation of blood using measurements of transmitted light.

3 Claims, 3 Drawing Sheets

5,687,719

1
PULSE OXIMETER PROBE

BACKGROUND OF THE INVENTION

1. Field of the Invention

The present invention relates to a pulse oximeter probe that detects the pulsation of blood in a blood vessel in the head of an intrauterine fetus for determining the oxygen saturation and other blood-related parameters in the time frame from the rupture of the water membrane to the delivery of the baby.

2. Related Art

Pulse oximeter probes are used to determine the oxygen saturation and other blood-related parameters by detecting the pulsation of blood in blood vessels in the human body. Conventional types have been attached to the foot, the hand or the earlobe of the object.

The operating principle of such conventional pulse oximeter probes is to measure the quantity of light that passes through the site of measurement as it is held between a light-emitting element and a light-receiving element. However, this is not suitable for the case where the target of measurement is a fetus in the process of delivery which can only be seen by the crown of the head as it comes out of the birth canal. In such a case, it is difficult to hold the site of measurement in proper position and, hence, considerable difficulty has been encountered in detecting the pulsation of fetal blood in the time frame from the rupture of the water membrane to the delivery of the baby.

SUMMARY OF THE INVENTION

The present invention has accomplished the object of providing a pulse oximeter probe that is capable of detecting the pulsation of blood in an intrauterine fetus for determining the oxygen saturation and other blood-related parameters in the birthing process from the rupture of the water membrane to the delivery of the baby.

This object can be attained by a pulse oximeter probe that illuminates the head of a fetus with light issuing from a light-emitting portion and which receives the transmitted or reflected light with a light-receiving portion for detecting the pulsation of blood in a blood vessel in the skin of said head, characterized in that an opening large enough to receive a part of the head of the fetus is formed in a curved support member of said probe and that said light-emitting and light-receiving portions are provided in said opening such a way that they face each other at a given spacing.

When the probe is inserted into the uterus until the support member slides under the head of a fetus, the support member, having a proper curvature, can be brought into intimate contact with the fetal head. Since an opening large enough to receive part of the fetal head is formed in the support member between light-emitting and light-receiving portions, the soft head can be positioned between those two photo-elements and this insures that the pulsation of blood flowing through a blood vessel in the head is detected with transmitted light.

2

Figure 1:
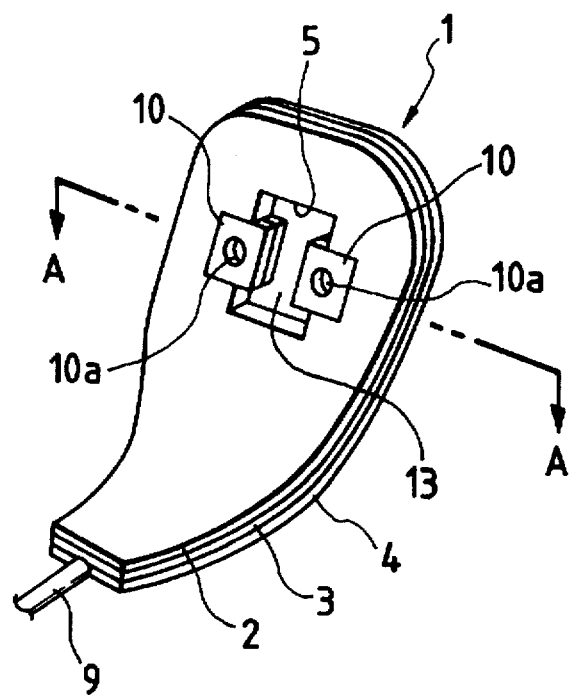
FIG. 1 is a perspective view showing the construction of a pulse oximeter probe according to an example of the present invention.
Figure 4:
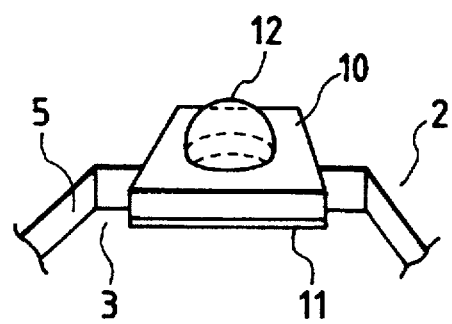
Figure 5:
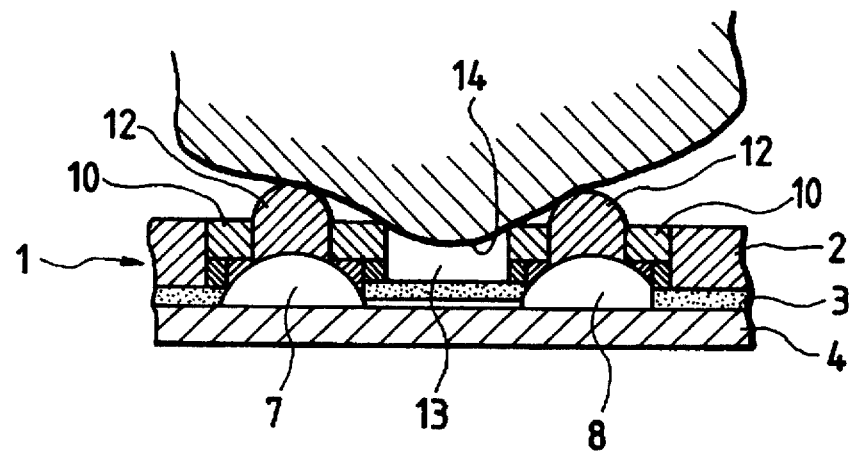

FIG. 4 is a partial enlarged view showing in perspective the thick silicon plate of FIG. 1 as it is filled with transparent silicon resin;

FIG. 5 is a sketch showing how the probe of FIG. 1 works during use; and

Figure 6:
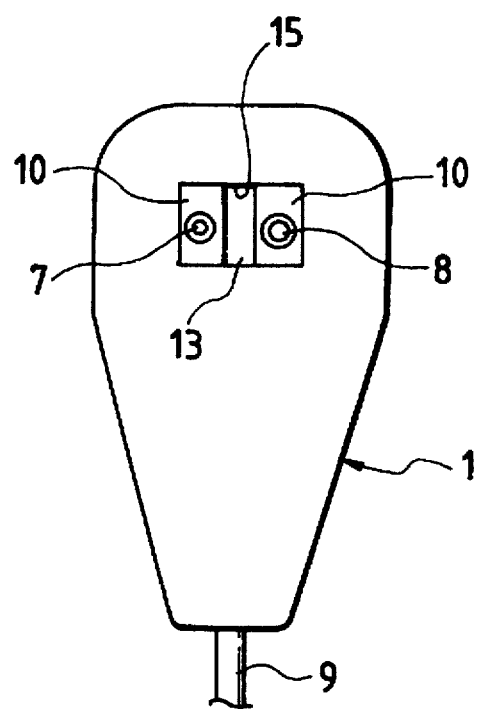

FIG. 6 is a plan view showing the construction of a pulse oximeter probe according to another example of the present invention.

DETAILED DESCRIPTION OF THE PREFERRED EMBODIMENTS

Examples of the pulse oximeter probe of the present invention are described below with reference to the accompanying drawings.

FIGS. 1 to 4 show the construction of a pulse oximeter probe according to an example of the present invention. Support member 1 is formed of a curved silicon sheet with blunt angles at the distal end and tapered at the proximal end. The support member 1 has a curvature equal to or less than that of the head of a fetus so that it will make intimate contact with the surface of the fetal head when the probe is inserted into the uterus. The support member 1 consists of three superposed silicon sheets 2, 3 and 4, with a cross-shaped opening 5 being formed in the upper silicon sheet 2. Round holes 6 are formed in the middle silicon sheet 3 in positions that coincide with two opposing sides of the opening 5. The silicon sheet 4 is black in color and has a light-shielding property in order to prevent the entrance of backlight that can disrupt light detection.

Figure 2:
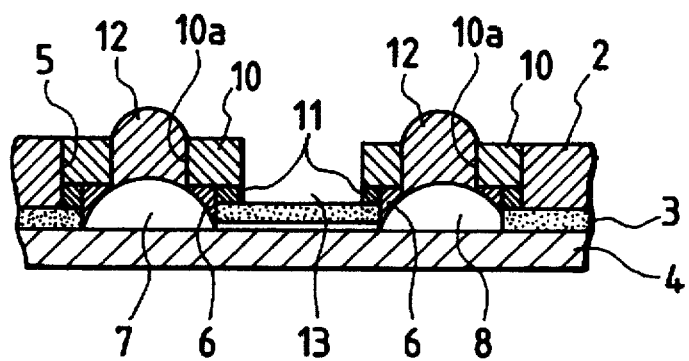
FIG. 2 is a cross section of FIG. 1 taken on line A—A.
Figure 3:
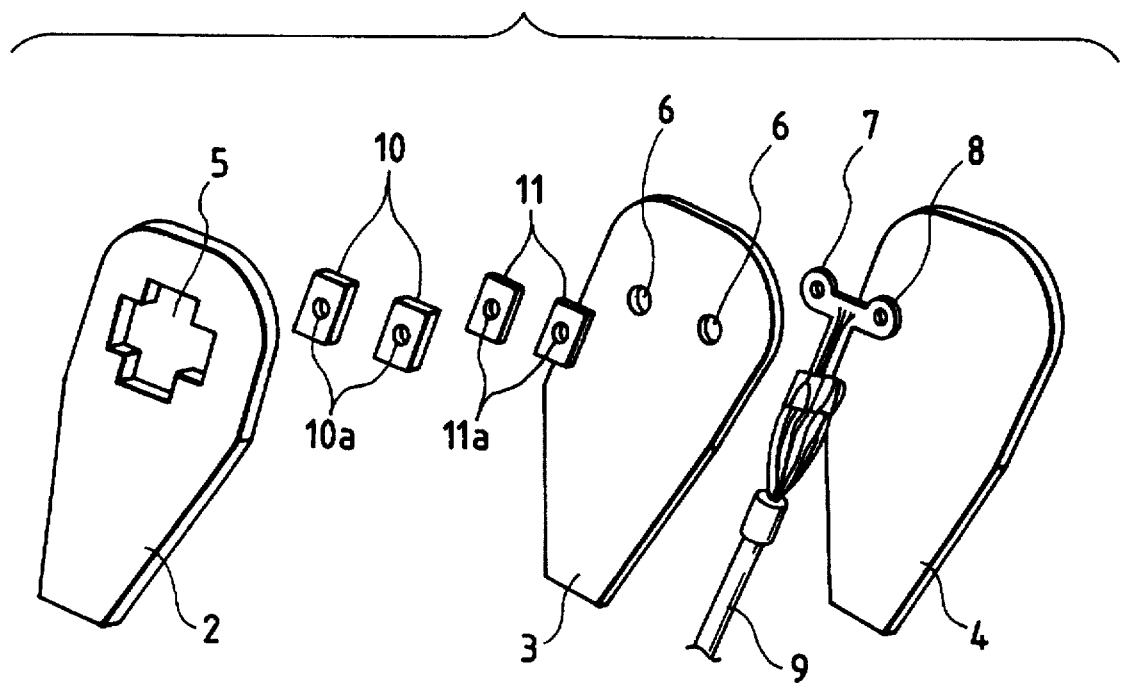
FIG. 3 is an exploded view of the pulse oximeter probe shown in FIG. 1.

A light-emitting element 7 and a light-receiving element 8 are each connected to a lead wire 9. The light emitter and receiver are held between silicon sheets 3 and 4 together with lead wire 9 as they are fitted in round holes 6 formed in the silicon sheet 3. For the sake of convenience in manufacturing, a thick rectangular shape, are fitted and bonded in superposition in the two opposing recesses of the opening 5 formed in the silicon sheet 2. Round holes 10a and 11a are formed in the centers of silicon plates 10 and 11, respectively, so that the tips of the light emitting element 7 and the light-receiving element 8 will be fitted in those round holes. As shown in FIGS. 2 and 4, each of the round holes 10a and 11a is filled with transparent silicon resin 12 which is raised upward to ensure that the optical path will not be blocked by hairs on the head of the fetus or the vernix caseosa.

The upper silicon sheet 2 and the thick silicon plate 10 each has a black rough surface so as to prevent the entrance of light noise or random reflection of light. The light emitter 7 and the light receiver 8 are connected to an external measuring circuit (not shown) via the lead wire 9. A gap 13 is formed between pair-forming thick silicon plates 10, as well as between pair-forming thin silicon plates 11.

The pulse oximeter probe of the example under consideration is used in the following manner. To begin with, the support member 1 is inserted into the uterus, with the round distal end advancing first, until it comes to the appropriate position under the head of a fetus, where the curved portion of the member 1 is brought into intimate contact with the head of the fetus under the pressure of the inner wall of the uterus. Since there is gap 13 between the light-emitting element 7 and the light-receiving element 8, part of the head 14 of the fetus rests between these elements and the light issuing from the element 7 passes through the transparent silicon resin 12, then through the skin of the head 14 to enter the element 8 to receive the transmitted light. The transmitted light helps in the detection of the pulsation of blood in a blood vessel in the head for measurement of the oxygen saturation, pulse waves, pulse rate and other blood-related parameters. With the tapered proximal end, the support member 1 will not make frequent contact with the inner wall of the birth canal even if the fetus moves through it under rotation during the birthing process from rupture of the water membrane to the delivery of the baby, and there is little possibility of displacement of the support member 1 from the head of the fetus. It should also be mentioned that since the silicon plates 10 around the tips of the light-emitting element 7 and the light-receiving element 8 have a black rough surface, there is no possibility that light issuing from the light-emitting element 7 undergoes random reflection.

In the example just described above, the curved support member 1 has the light-emitting element 7 and the light-receiving element 8 which are spaced from each other by the gap 13. Because of this arrangement, the pulsation of blood flowing in an intrauterine fetus can be easily detected in the birthing process from the rupture of the water membrane to the delivery of the baby, whereby the oxygen saturation and other parameters of the blood can be measured.

The shape of the opening 5 is in no way limited to the case shown in connection with the foregoing description of the first example of the present invention. If desired, a rectangular shape may be employed as shown by opening 15 in FIG. 6, with the light-emitting element 7 and the light-receiving element 8 being positioned along two opposing sides of the opening 15 in a face-to-face relationship as they are spaced apart by gap 13 that is large enough to receive part of the head of a fetus. Another modification in design that can be adopted is to spherically shapen the tip of the transparent silicon sheet 12 which is packed in holes 10a and 11a. This is effective in reducing the friction that develops between the support member 1 and the inner wall of the uterus as the support member 1 is inserted into the inner wall of the uterus.

As described above, the pulse oximeter probe of the present invention has an opening formed in the support member that is curved with a curvature almost comparable to that of the head of a fetus and, in addition, a light-emitting and a light-receiving portion are positioned in a face-to-face relationship within the opening. Because of this construction, the probe is capable of easily determining the oxygen saturation and other parameters of blood flowing in a fetus in the uterus by detecting the pulsation of the blood in the time frame from the rupture of the water membrane to the delivery of the baby.

What is claimed is:

1. A pulse oximeter probe comprising:

a light emitting element for emitting a light to a head of a fetus;

a light receiving element for receiving from said light emitting element at least one of transmitted light and reflected light to detect the pulsation of blood in the fetus; and a supporting member with a predetermined curvature, the supporting member having an opening wherein the light emitting element and the light receiving element are positioned in the opening to form a gap between the light emitting element and the light receiving element to receive a portion of the head of the fetus, wherein the supporting member comprises a plurality of laminated silicon sheets wherein one of the silicon sheets has a black rough surface.

2. A pulse oximeter probe comprising:

a light emitting element for emitting a light to a head of a fetus;

a light receiving element for receiving from said light emitting element at least one of transmitted light and reflected light to detect the pulsation of blood in the fetus; and a supporting member with a predetermined curvature, the supporting member having an opening wherein the light emitting element and the light receiving element are positioned in the opening to form a gap between the light emitting element and the light receiving element to receive a portion of the head of the fetus;

a first and second silicon plate positioned in the opening of the supporting member, wherein each silicon plate has a hole and the light emitting element is aligned with the hole of the first plate and the light receiving element aligned with the hole of the second plate, each silicon plate has a black rough surface, and the holes contain a transparent resin.

3. A pulse oximeter comprising:

a light emitting element for emitting light to a head of a fetus;

a light receiving element for receiving from said light emitting element at least one of transmitted light and reflected light to detect the pulsation of blood in the fetus;

a first silicon plate containing a hole wherein the light emitting element is aligned with the hole and the hole contains a transparent resin;

a second silicon plate containing a hole, wherein the light receiving element is aligned with the hole and the hole contains a transparent resin; and a tapered support member with a predetermined curvature not greater than the curvature of a head of a fetus; wherein said supporting member comprises a plurality of laminated silicon sheets and has an opening in which the first and second silicon plates are positioned to form a gap to receive a portion of the head of the fetus.

* * * * *